US009238833B2

(12) United States Patent
Chen et al.

(10) Patent No.: US 9,238,833 B2
(45) Date of Patent: Jan. 19, 2016

(54) THERMALLY CONTROLLED CHAMBER WITH OPTICAL ACCESS FOR HIGH-PERFORMANCE PCR

(71) Applicant: CALIFORNIA INSTITUTE OF TECHNOLOGY, Pasadena, CA (US)

(72) Inventors: Samson Chen, Flushing, NY (US); Aditya Rajagopal, Irvine, CA (US); Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 194 days.

(21) Appl. No.: 14/028,431

(22) Filed: Sep. 16, 2013

(65) Prior Publication Data

US 2014/0080133 A1    Mar. 20, 2014

Related U.S. Application Data

(60) Provisional application No. 61/702,111, filed on Sep. 17, 2012.

(51) Int. Cl.
| | |
|---|---|
| *C12Q 1/68* | (2006.01) |
| *C12P 19/34* | (2006.01) |
| *H05K 3/46* | (2006.01) |
| *H05K 1/02* | (2006.01) |
| *H05K 1/16* | (2006.01) |
| *B01L 7/00* | (2006.01) |

(52) U.S. Cl.
CPC . *C12Q 1/686* (2013.01); *B01L 7/52* (2013.01); *H05K 1/0212* (2013.01); *H05K 1/0272* (2013.01); *H05K 1/16* (2013.01); *H05K 3/4644* (2013.01); *H05K 3/4697* (2013.01); *B01L 2200/12* (2013.01); *B01L 2300/0877* (2013.01); *B01L 2300/1827* (2013.01); *Y10T 29/49155* (2015.01)

(58) Field of Classification Search
CPC ....... C12Q 1/686; B01L 2200/12; B01L 7/52; B01L 2300/0877; B01L 2300/1827
See application file for complete search history.

(56) References Cited

U.S. PATENT DOCUMENTS

| | | | |
|---|---|---|---|
| 5,804,881 | A | 9/1998 | Wille et al. |
| 6,786,708 | B2 | 9/2004 | Brown et al. |
| 8,220,487 | B2 | 7/2012 | Unger et al. |
| 8,243,358 | B2 | 8/2012 | Wen et al. |
| 8,372,726 | B2 | 2/2013 | De Graff et al. |
| 8,382,896 | B2 | 2/2013 | Hansen et al. |
| 2004/0013545 | A1 | 1/2004 | Brown et al. |
| 2007/0095879 | A1 | 5/2007 | Holmes |
| 2008/0038163 | A1 | 2/2008 | Boege et al. |
| 2008/0057627 | A1 | 3/2008 | Chang |
| 2008/0101044 | A1 | 5/2008 | Chang |
| 2012/0264202 | A1* | 10/2012 | Walker ............. B01L 3/502707 435/287.2 |

OTHER PUBLICATIONS

Lee, Dae-Sik et al., "A Disposable Plastic-Silicon Micro PCR Chip Using Flexible Printed Circuit Board Protocols and Its Application to Genomic DNA Amplification", IEES Sensors Journal, vol. 8, No. 5, May 2008, pp. 558-564.
Restriction Requirement mailed on Mar. 15, 2013 for U.S. Appl. No. 13/448,810 filed in the name of Samson Chen on Apr. 17, 2012.
Notice of Allowance mailed on Aug. 16, 2013 for U.S. Appl. No. 13/448,810 filed in the name of Samson Chen on Apr. 17, 2012.
Notice of Allowance mailed on Jan. 7, 2014 for U.S. Appl. No. 14/038,702 filed in the name of Samson Chen on Sep. 26, 2013.
Restriction Requirement mailed on Sep. 30, 2014 for U.S. Appl. No. 13/763,352 filed in the name of Aditya Rajagopal on Feb. 8, 2013.
Non-Final Office Action mailed on Mar. 17, 2015 for U.S. Appl. No. 13/763,352 filed in the name of Aditya Rajagopal on Feb. 8, 2013.
PCT International Search Report mailed on Oct. 24, 2012 for PCT Application No. PCT/US2012/033914 filed on Apr. 17, 2012 in the name of California Institute of Technology et al.
PCT Written Opinion mailed on Oct. 24, 2012 for PCT Application No. PCT/US2012/033914 filed on Apr. 17, 2012 in the name of California Institute of Technology et al.

* cited by examiner

*Primary Examiner* — Young J Kim
(74) *Attorney, Agent, or Firm* — Steinfl & Bruno LLP

(57) ABSTRACT

Novel methods and systems for polymerase chain reaction (PCR) are disclosed. A PCR device has a bottom heater layer, a central reacting layer, and a top heater layer. The central reacting layer has a PCR reacting chamber connected with fluidics channels. Photoluminescence of a DNA solution in the PCR reactive chamber is carried out through the transparent top layers.

11 Claims, 3 Drawing Sheets

THERMALLY CONTROLLED CHAMBER WITH OPTICAL ACCESS FOR HIGH-PERFORMANCE PCR

CROSS REFERENCE TO RELATED APPLICATIONS

The present application claims priority to U.S. Provisional Patent Application No. 61/702,111, filed on Sep. 17, 2012, and may be related to U.S. patent application Ser. No. 13/763,352, filed on Feb. 8, 2013, and U.S. patent application Ser. No. 13/448,810, filed on Apr. 17, 2012, the disclosure of all of which is incorporated herein by reference in their entirety.

TECHNICAL FIELD

The present disclosure relates to the detection and analysis of biological entities. More particularly, it relates to polymerase chain reaction (PCR) systems and methods.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
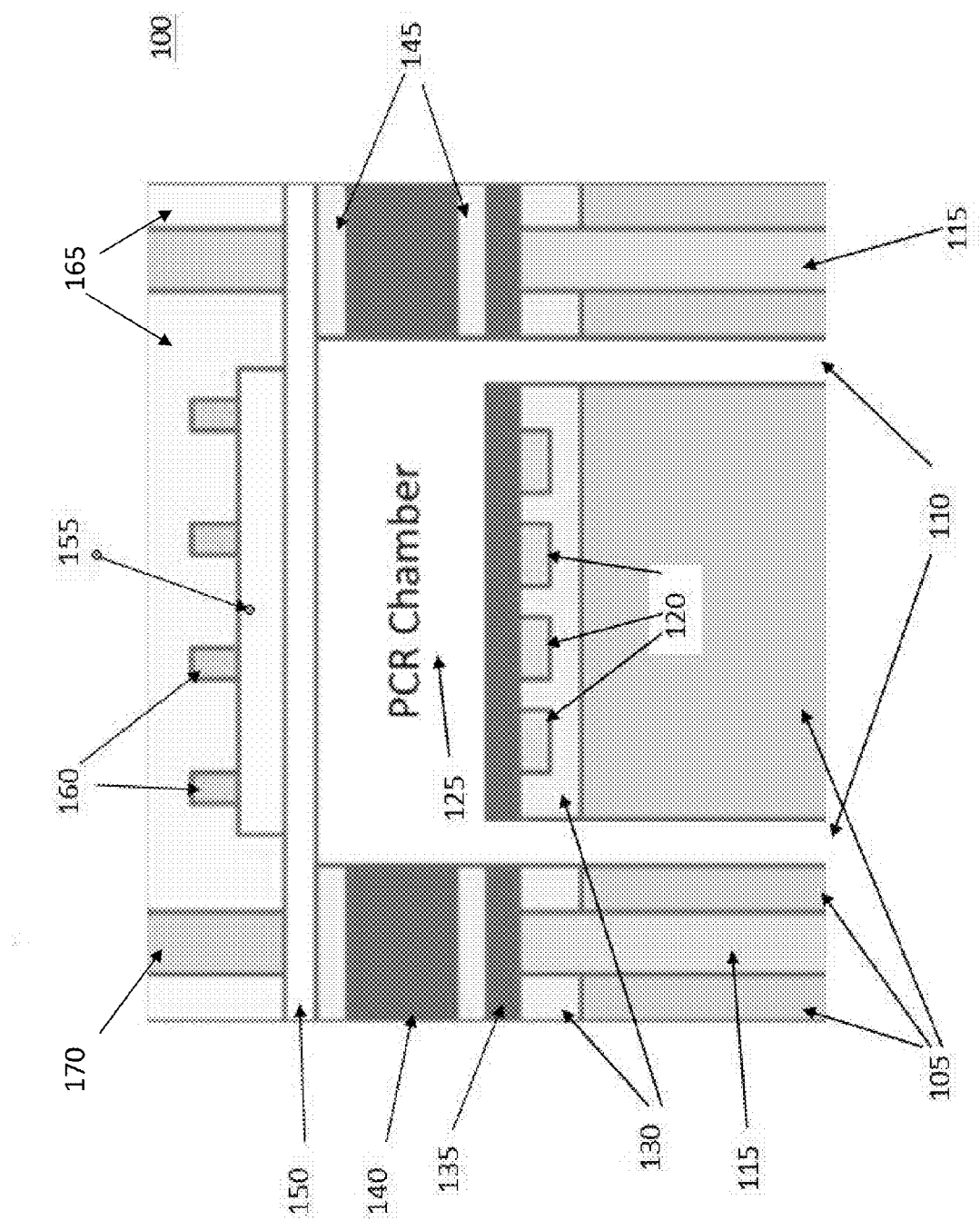
FIG. 1 depicts an exemplary PCR chamber device.

In a first aspect of the disclosure, a device is described, the device comprising: a bottom heater layer, wherein the bottom heater layer comprises a bottom substrate layer, a first adhesive layer, heater elements, a top substrate layer, and fluidics channels; a central reacting layer, wherein the central reacting layer comprises a fluidics chamber connected to the fluidics channels; and a top heater layer, the top heater layer comprising a transparent insulating layer, a transparent conducting layer, a digitated conducting layer, and a top protective layer, wherein the transparent insulating layer is connected to the central reacting layer; wherein the bottom heater layer is bonded to the central reacting layer with a second adhesive layer, and the central reacting layer is bonded to the top heater layer with a third adhesive layer.

In a second aspect of the disclosure, a method for fabricating a device is described, the method comprising: fabricating heater elements; bonding the bottom heater elements to a bottom substrate through a first adhesive layer or through wafer bonding; fabricating a top substrate on the heater elements; defining fluidics channels through the bottom substrate, the first adhesive layer, and the top substrate; defining a central reacting chamber in a central layer; bonding the central reacting chamber to the top substrate, in such a way as to connect the central reacting chamber to the fluidics channels; fabricating a transparent insulating layer; fabricating a transparent conducting top heater layer; fabricating a digitated conductive layer; depositing a protective layer; and bonding the central reactive chamber to the transparent insulating layer.

In a third aspect of the disclosure, a method for processing polymerase chain reactions is described, the method comprising: providing the device of claim 1; injecting a DNA solution in the fluidics chamber through the fluidics channels; illuminating the fluidics chamber with a light source through the top heater layer; and detecting photoluminescence through the top heater layer.

DETAILED DESCRIPTION

Polymerase Chain Reaction (PCR) is a well-known biological analysis technique which may be used to amplify and permit the detection of specific sequences of DNA. This technique has been suggested for use in point-of-care medical applications. However, standard implementations of PCR are too costly or not portable enough for such applications. From an instrumentation standpoint, the most difficult part of PCR is usually related to the thermal characteristics of the system, as the performance of a PCR reaction is typically very dependent on good temperature control and regulation. Additionally, in sample-to-answer applications an optically transparent chamber is often necessary to permit simultaneous detection of the results of the PCR reaction.

The use of printed circuit board (PCB) systems and methods for PCR was described in U.S. Ser. No. 13/763,352 and U.S. Ser. No. 13/448,810, the disclosure of both of which is incorporated herein by reference in their entirety. The use of such PCB systems allows handling both electrical signals and fluidics in a single assembly, thereby significantly reducing the cost and size of a variety of biological applications, such as PCR. The fluidics parts of the disclosure may be fabricated, for example, by mechanical, laser, water jet, electron discharge or ion cutting, mechanical, laser or ion milling, lithography, chemical etching.

In the present disclosure, a PCB-based thermal and fluidic assembly is described. Such assembly is designed to optimize the thermal performance of the fluidics chamber while permitting optical interrogation of a PCR sample. More generally, the present disclosure describes the integration, on one hand, of optically transparent materials typically used in electronic screen printing and display applications, and, on the other hand, of PCB fluidics applications.

PCR is a technique which amplifies a particular sequence of DNA to measurable quantities. In order to actually determine whether or not that sample of DNA was actually originally present in the sample, it is necessary to find a way to quantify the amount of DNA in the sample. Many of the well-established methods of quantifying DNA concentration rely on using fluorescent probes. These methods typically involve the excitation of fluorophores, bound to the DNA in the solution, with UV light, and measurement of any emitted visible light. The transparent chamber in the present disclosure permits measurement of the emitted light, without the need of a fluidic step which would move the PCR reactants away from the chamber for optical analysis. Additionally, by making the chamber itself transparent, real-time PCR and other methods which require quantification of amplified DNA during the process become possible.

Providing fast and uniform temperature control is integral to high quality and high performance PCR results. The temperature steps in PCR are exceptionally sensitive and a fraction of a degree error or nonuniformity can drastically reduce the yield of a PCR reaction or worse yet, create false PCR results. The single heater design described in the previous disclosure cited above (U.S. Ser. No. 13/763,352) is already capable of very high thermal performance, thanks to the thin PCR chamber and the small thermal separation between sample and heater afforded by thin PCB-based construction. However, in certain circumstances, there exists the possibility that a thermal gradient develops across the chamber in the solution. To obviate this potential problem, it may be advantageous, as described in the present disclosure, to sandwich the PCR chamber between two heaters. Delivering equal amounts of power to both heaters can then drastically improve the thermal uniformity of the chamber. As described in some embodiments of the present disclosure, the use of transparent conductors such as indium tin oxide (ITO), on top of a transparent film, can make the use of dual heaters possible, while preserving the transparency of the PCR chamber itself.

FIG. 1 illustrates an exemplary embodiment of a PCR chamber device (100). The structure of the device (100) is defined by several layers of standard flex PCB materials and several additional layers of transparent materials.

As visible in FIG. 1, a rigid support layer (105) is present to increase the structural strength of the device (100). Inlets (110) permit the intake of fluids into the device (100). Copper heater vias (115) are present. A copper heater layer comprises copper elements (120). The elements (120) are close to a PCR chamber (125), permitting the controlled heating of chamber (125) during the PCR process. The elements (120) are joined to the rigid support (105) through a bonding layer (130). Layer (130) could be made, for example, by standard acrylate glue, for flexibility (flex support).

The chamber (125) is separated from the heaters (120) by a layer of, for example, Kapton (135). Kapton is a polyimide film known to the person skilled in the art. Other materials may be employed instead, as understood by the person skilled in the art. For example, co-polymers (such as COC, cyclic oleofin copolymer) or polyethylene or silicon dioxide (glass). The chamber (125) is also formed as an empty space inside several layers of Kapton (140).

Adhesive layers (145) can be used to join the lower Kapton layer (135) to the upper Kapton layers (140), as well as to join the upper Kapton layers (140) to a transparent insulating substrate layer (150). Layer (150) may be fabricated, for example, from thermally stabilized polyethylene terephthalate (PET) or polyethylene naphthalate (PEN). Other insulating transparent materials could be used for layer (150), such as aluminum oxide or silicon nitride or silicon dioxide or silicon. Adhesive layers (145) may be actually adhesives, or may be instead fabricated by wafer bonding at a suitable combination of pressure and temperature, as understood by the person skilled in the art. In some embodiments, a polymerase chain reaction polymer may be used, as understood by the person skilled in the art.

A transparent conducting upper heater layer (155) is deposited on top of the transparent insulator (150). Layer (155) may be fabricated, for example, with ITO, graphene, polyethylene dioxythiphene (PEDOT), PEN, or other similar materials as understood by a person skilled in the art. For example, layer (155) could also be made of a semitransparent (referred to as transparent in the present disclosure) thin layer of gold, silver, copper, silicon or a doped semiconductor. Layer (155) may be fabricated, for example, by sputtering, evaporation, wafer bonding, or chemically- or ion-assisted-deposition. A heater bus made of several elements (160) contacts layer (155) to conduct a current necessary for the heater operation. Layer (160) may be fabricated from copper, silver, or other conducting materials.

A protective layer (165) may be fabricated, for example, from PET or other protectants such as screen-printable protectants. Layer (165) is designed to leave parts of layer (160) accessible (these accessible parts are shown in FIG. 1 as element 170) in order to inject the necessary electrical current.

As can be noted by the person skilled in the art, the top screen-printing based layers (150, 155, 160, 165) borrow a number of features most commonly seen in electronic screen printing. In particular, most of the materials which can be used to fabricate layers (150, 155, 160, 165) are commonly employed in electroluminescent lamp manufacture, and are well-established in the field. Most of these materials can be formed additively: for example, pastes are deposited through a defined screen and thermally cured to produce layers (150, 155, 160, 165). The exception is ITO, which is a transparent conductor typically sputtered onto a substrate, as known to the person skilled in the art.

Because most transparent conductive materials which can be used as heater elements (such as 155 in FIG. 1) have relatively high resistivity compared to copper, an entire solid layer of conductor is used, instead of a number of separate elements. When seen from the top of a PCR device, the heater element (155) will comprise a solid and continuous area.

Figure 2:
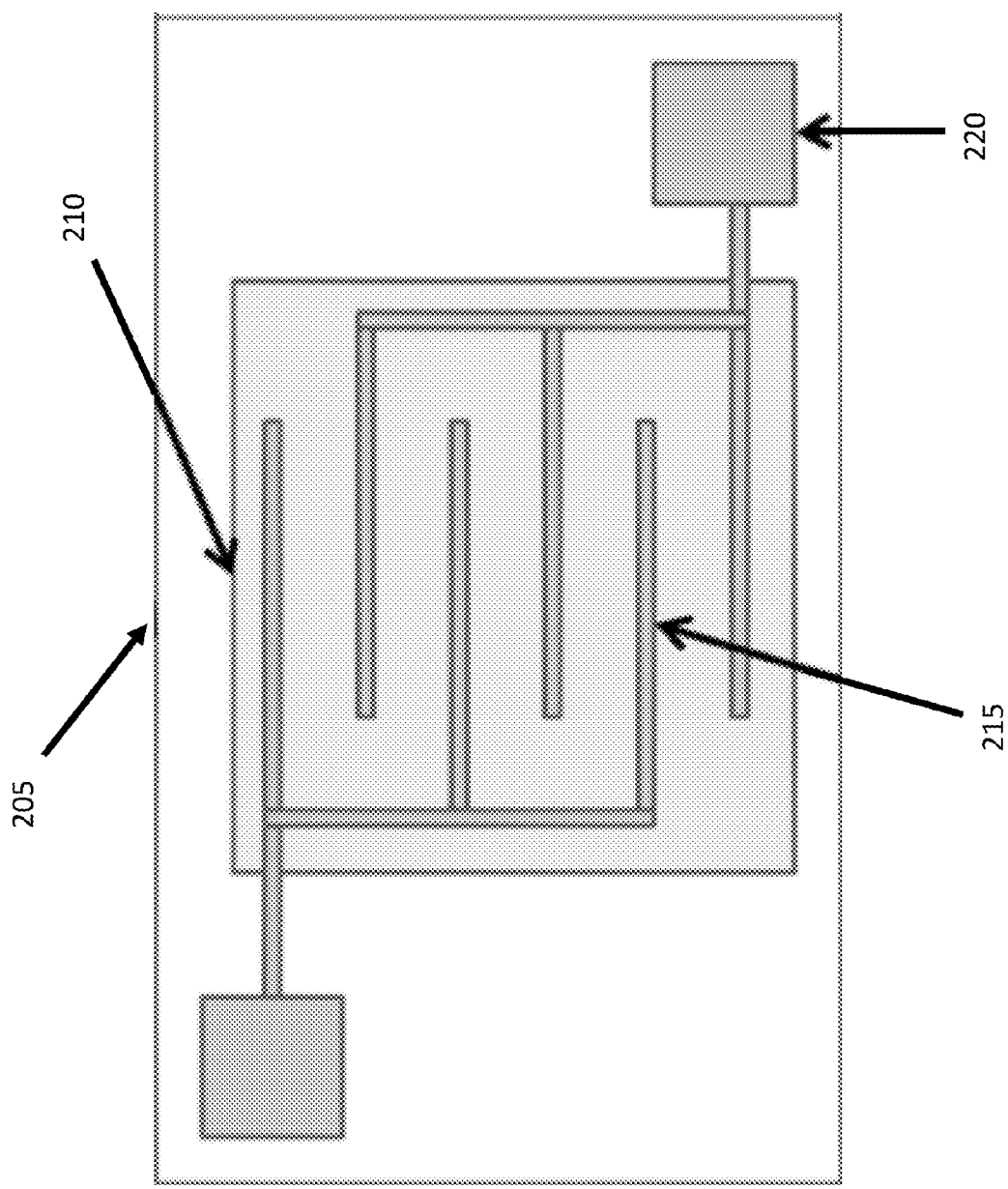
FIG. 2 depicts a top view of an exemplary PCR chamber device.

FIG. 2 illustrates a top view of an exemplary PCR device, such as the device of FIG. 1. Referring to FIG. 2. A transparent insulating layer (205) can be fabricated, for example, from PET. Layer (205) in FIG. 2 corresponds to layer (150) in FIG. 1.

Referring again to FIG. 2, a transparent conductor layer (210) can be fabricated, for example, from ITO, graphene, polyethylene dioxythiphene (PEDOT), or PEN. Layer (210) in FIG. 2 corresponds to layer (155) in FIG. 1.

Referring again to FIG. 2, a layer with high conductivity (215) can be fabricated, for example, from copper or silver. Layer (215) in FIG. 2 corresponds to layer (160) in FIG. 1.

Referring again to FIG. 2, layer (215) can have a digitated shape. This shape can be advantageous for reasons explained later in the present disclosure. A digitated layer may be fabricated, for example, by stencil masking or screen printing.

Referring to FIG. 1, in order to ensure the same heat output from the two heater layers (120) and (155), where layer (120) is the bottom heater layer and layer (155) is the top heater layer, the two heater layers (120,155) can have similar resistances in some embodiments.

As an example, in approximately a square inch area, serpentine copper heaters typically have, at most, a resistance of 1-10 Ohms. This is due to the typical limits of the fabrication process (the minimum line width). Copper is an exemplary material for bottom heater layer (120).

On the other hand, for most conductive transparent materials (such as those employed for layer 155), the above resistance range of 1-10 Ohms is on the very low end of possible resistance values. Such values are typically obtained, for conductive transparent materials, by depositing very thick layers. Due to the thickness of the layers, low resistance transparent conductors are typically very expensive and have significant optical loss. The optical loss is due to the light having to traverse a greater thickness of material.

In order to overcome the resistance mismatch and related adverse consequences, a second, thin layer with high conductivity, such as a layer of silver ink, may be deposited onto layer (155) or FIG. 1, or layer (210) of FIG. 2. Such thin layer can be visible in FIG. 1 as layer (160) or in FIG. 2 as layer (215).

Referring now to FIG. 2, by forming a digitated structure (215) on top of the transparent conductor (210), the overall resistance of layers (215) and (210) can be reduced, while still utilizing the entire area available to the heater for heating (the area of layer 210). Because the opaque layer (215) has a high conductivity, it is possible to deposit extremely narrow lines which, in actuality, do not greatly reduce the viewable area of the PCR chamber. Layer (215) connects to contact pads (220).

As can be understood from the above description, an exemplary embodiment of the PCR devices of the present disclosure can comprise a group of top layers and a group of bottom layers.

For example, referring now to FIG. 1, layers (150,155,160, 165,170) are the group of top layers, the top portion of the PCR device (100). Layers (135,130,120,115,105) are the group of bottom layers, the bottom portion of the PCR device (100). The central portion comprises layer (140). Adhesive layers (145) join the bottom layers (135,130,120,115,105) to the central portion (140), and the central portion (140) to the top layers (150,155,160,165,170). Adhesive layers (145) can be fabricated, for example, with acrylic adhesive using standard flex PCB fabrication techniques. Other adhesives may be used as well, as understood by the person skilled in the art.

All of the bottom PCB-based layers (135, 130, 120, 115, 105) may be fabricated using standard flex PCB fabrication techniques. Individual layers made of copper (such as layer 120) can have their traces defined using standard photolithographic processes and etching. Thicker fluidic channels defined in the substrate material can be laser cut or milled. The fabrication of thinner fluidic channels can be defined by a PCB trace which is etched away through a PCB via, after final assembly of the PCR device (100).

The top PCB-based layers may be fabricated using techniques well known to the display industry and electronic screen printing industry. In some specialty applications, such as keypad manufacture, specialty PCBs are used, employing additive screen printing on films, to define structures. As known to the person skilled in the art, in screen printing a fine mesh is coated with a photosensitive emulsion, which is exposed to produce a pattern of openings. Specialty inks are then forced through these holes, which is then typically cured thermally or with UV light.

As known to the person skilled in the art, silkscreen legends and solder masks on PCBs used to be produced with the above technique, but have been largely replaced by photosensitive dry films. In keypad contact manufacture and some other PCB applications, resistors and conductors can be produced by screen printing conductors onto a substrate.

In the display industry, transparent substrates and conductors are integral due to the need to route signals to individual pixels while maintaining optical transparency. Transparent conductors, such as ITO, are thus very commonly used. ITO is typically sputtered onto a substrate (glass for LCDs, or PET plastic in some other display applications). This is done either through a mask or without a mask, and etched afterwards through a standard photolithographic process. A relevant process to the fabrication methods of several embodiments of the present disclosure is derived from electroluminescent (EL) display fabrication.

In EL displays, light is actively emitted by exciting an electroluminescent phosphor with a high voltage AC signal. This phosphor typically needs to be sandwiched between an additional dielectric layer and two conductors. The side which emits light must be transparent and conductive, so the ITO-coated PET substrate is usually on that side. In some extremely cost-sensitive applications, a lower conductivity, lower-transparency PEDOT conductive polymer may be screen printed for this layer. The layers of phosphor, dielectric, rear electrodes (often carbon or silver ink depending on conductivity requirements), and protective encapsulation layer are then screen printed to form the EL assembly.

In several embodiments of the present disclosure, many of the above techniques can be used together with techniques used in EL lamp assembly. For example, by screen printing a transparent conductive layer, or starting with an ITO-sputtered PET film layer, and subsequently screen printing conductors, in order to make contacts or modify the resistance of the transparent heater (such as layer 155 in FIG. 1).

In several embodiments, the material which directly contacts the PCR reactor is the PET film, which has been shown to be compatible with PCR processes.

In other embodiments, a wafer-bonded structure could be used, for example a silicon on insulator structure. Such structure can be used to define small fluid volumes, in which a conducting semiconducting layer is transparent to a degree. For example, semiconductors such as silicon (and silicon dioxide), aluminum nitride or gallium nitride could be used.

Referring to adhesive layers (145), the entire transparent heater and PCB assembly may be adhered to with standard multilayer flex fabrication techniques. All of the layers (145) could be laminated with B-staged acrylic adhesives. As known to the person skilled in the art, these exemplary adhesives are basically two-part adhesives that have been mixed, deliberately "paused" before full cure, and formed into continuous thin sheets. These adhesive have been designed to be fully cured with heat and pressure.

A possible difficulty in the fabrication of the PCR devices of the present disclosure comes from the fact that PET cannot easily withstand the same temperatures that Kapton and other PCB materials can withstand. The grade of PET typically used in screen printing is very high temperature, as many of the curing steps require exposure to high temperatures (130° C. or more) without damage to the PET layer. However, typical soldering steps require intermittent exposure to upwards of 200° C.

Additionally, standard B-staged adhesives used in PCB assembly are designed to work with higher temperatures (also about 200° C.), though this is primarily in order to increase the shelf life of B-staged adhesives for manufacturers (the higher the cure temperature, the less the adhesive will "go bad" by curing at room temperature). Most B-staged adhesive films used outside the industry in fact use much lower temperatures compatible with PET. Thus, lamination of the PET layer with a lower temperature B-staged adhesive may have to be done after complete lamination of the PCB layers and soldering of any mounted components. Alternatively, the PET layer may be adhered to using a room-temperature curing pressure sensitive adhesive (tape, basically) or dispensed liquid adhesive, as understood to the person skilled in the art.

Figure 3:
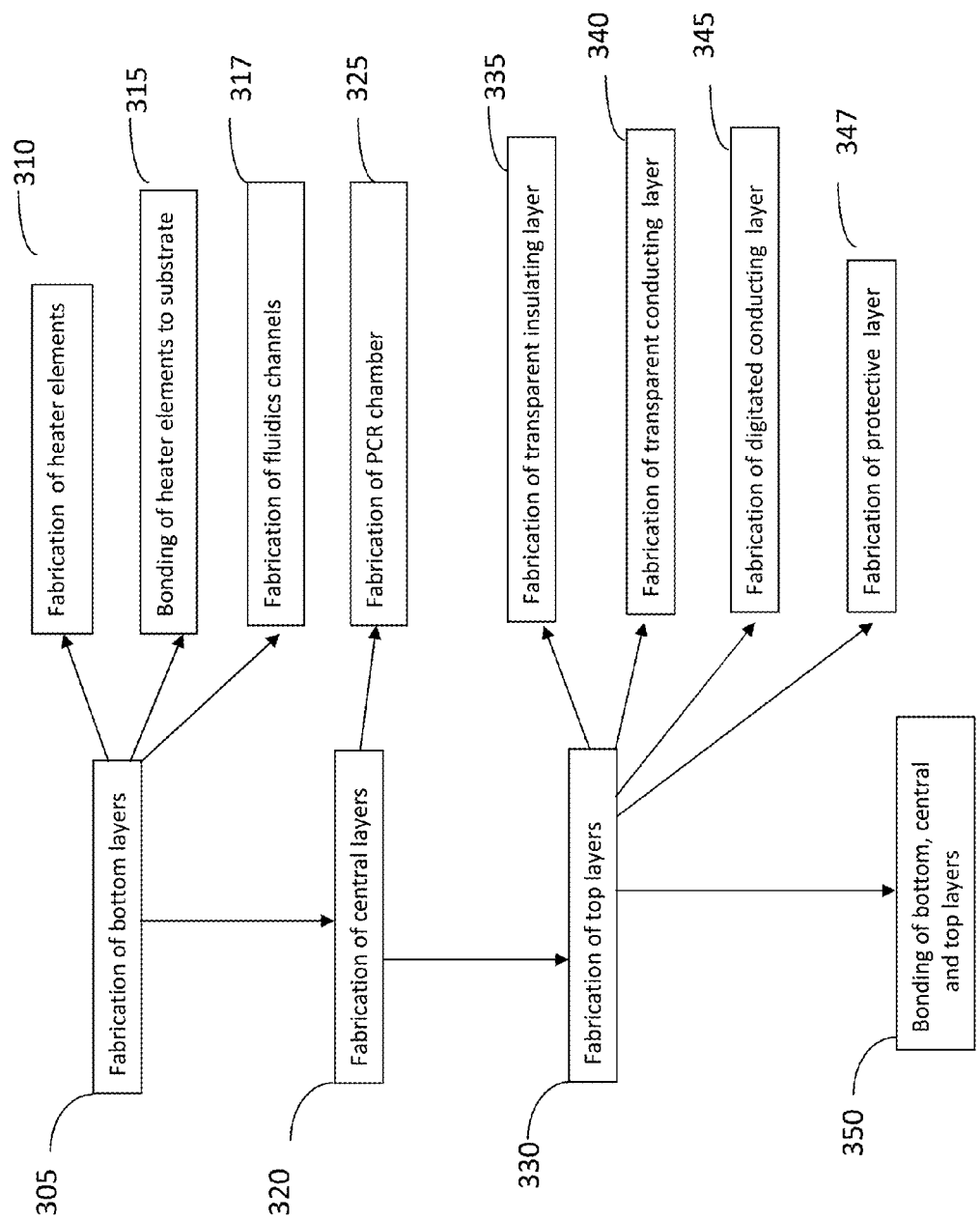
FIG. 3 illustrates a method of fabrication of a PCR chamber device.

Accordingly, a method for fabricating a PCR chamber device would comprise the following steps, as illustrated in FIG. 3.

In a first step (305), the bottom layers of the PCR chamber device are fabricated, using standard flex PCB fabrication techniques. Step (305) comprises the fabrication of heater elements (310), for example by standard photolithography and etching processes. The heater elements might be fabricated (310) directly on a support substrate, or may be subsequently bonded to a substrate (315) instead. The heater elements might also be attached to a support layer which separates them from the central portion of the PCR device, such as a Kapton layer. Step (305) also comprises the fabrication of fluidics channels (317) to connect to the central PCR chamber. The fluidic channels may be fabricated, for example, by laser cutting, milling, or etching.

In a next step (320), the central layers are fabricated. Step (320) comprises the fabrication of the central PCR chamber (325), for example using Kapton layers.

In a next step (330), the top layers are fabricated, using standard techniques commonly used in the display industry and in the electronic screen printing industry. Step (330) comprises the fabrication of a transparent insulating layer (335), and a transparent conducting layer (340), which acts as an upper heater. Step (330) further comprises the fabrication of a digitated conducting layer (345). Steps (335,340,345) may be carried out, for example, by screen printing, sputtering, and photolithography. Step (330) further comprises the fabrication of a protective layer (347).

In a next step (350), the bottom, central and top layers are bonded, for example by using adhesive such as acrylate glues or other adhesives compatible with PCR amplification.

The person skilled in the art will understand that, although a geometry with a transparent top heater layer was described in some embodiments of the disclosure, in other embodiments the bottom layers may be switched with the top layers, so that the bottom layer may be transparent. Therefore, every layer which is referred to as a top layer in the present disclosure may become a bottom layer in other embodiments of the present disclosure. Accordingly, every layer which is referred to as a bottom layer in the present disclosure may become a top layer in other embodiments of the present disclosure.

Although several embodiments of the devices described in the present disclosure has been designed for PCR processes, the person skilled in the art will understand that other processes which require a similar set of features may also advantageously use some embodiments of the devices of the present disclosure, therefore it should be understood that the use of PCR as an example should not be intended as a limitation for the applications of the devices of the present disclosure.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art a complete disclosure and description of how to make and use the embodiments of the gamut mapping of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A device comprising:
    a bottom heater layer, wherein the bottom heater layer comprises a bottom substrate layer, a first adhesive layer, heater elements, a top substrate layer, and fluidics channels;
    a central reacting layer, wherein the central reacting layer comprises a fluidics chamber connected to the fluidics channels; and
    a top heater layer, the top heater layer comprising a transparent insulating layer, a transparent conducting layer, a digitated conducting layer, and a top protective layer, wherein the transparent insulating layer is connected to the central reacting layer;
    wherein the bottom heater layer is bonded to the central reacting layer with a second adhesive layer, and the central reacting layer is bonded to the top heater layer with a third adhesive layer.

2. The device of claim 1, wherein the first adhesive layer is made of an acrylate glue, the heater elements are made of copper, and the top substrate layer is a polyimide film.

3. The device of claim 1, wherein the central reacting layer comprises layers made of one of the following materials: polyimide, cyclic oleofin copolymer, polyethylene, a co-polymer or silicon dioxide.

4. The device of claim 1, wherein the transparent insulating layer is made of thermally stabilized polyethylene terephthalate, polyethylene naphthalate, aluminum oxide, silicon nitride, silicon dioxide or silicon.

5. The device of claim 1, wherein the transparent conducting layer is made of indium tin oxide, graphene, polyethylene dioxythiphene, polyethylene naphthalate, gold, silver, copper, silicon or a doped semiconductor.

6. The device of claim 1, wherein the digitated conducting layer is made of copper or silver or doped semiconductor such as silicon or gallium nitride or aluminum nitride.

7. The device of claim 1, wherein the first, second or third adhesive layers are made of acrylate glue, B-stage adhesives, or of a polymer compatible with polymerase chain reaction.

8. The device of claim 1, wherein the digitated conducting layer is thinner than the transparent conducting layer.

9. The device of claim 1, wherein the device is for polymerase chain reaction.

10. The device of claim 1, wherein the first, second or third adhesive layers are formed by wafer bonding at high pressures or temperatures or combinations thereof.

11. A method for processing polymerase chain reactions, the method comprising:
    providing the device of claim 1;
    injecting a DNA solution in the fluidics chamber through the fluidics channels;
    illuminating the fluidics chamber with a light source through the top heater layer; and
    detecting photoluminescence through the top heater layer.

* * * * *